US012678151B2

(12) United States Patent
Brenizer et al.

(10) Patent No.: US 12,678,151 B2
(45) Date of Patent: Jul. 14, 2026

(54) VASCULAR CLOSURE DEVICE WITH RETRACTION ASSEMBLY FOR REPOSITIONING A FOOTPLATE

(71) Applicant: Teleflex Life Sciences LLC, Wilmington, DE (US)

(72) Inventors: Joshua Brenizer, Oak Grove, MN (US); Darren Prom, Coon Rapids, MN (US); Christopher E. Buller, Toronto (CA); Nicholas Mark Donnay, Plymouth, MN (US)

(73) Assignee: Teleflex Life Sciences LLC, Wilmington, DE (US)

( * ) Notice: Subject to any disclaimer, the term of this patent is extended or adjusted under 35 U.S.C. 154(b) by 4 days.

(21) Appl. No.: 18/797,479

(22) Filed: Aug. 7, 2024

(65) Prior Publication Data

US 2025/0049426 A1     Feb. 13, 2025

Related U.S. Application Data

(60) Provisional application No. 63/517,979, filed on Aug. 7, 2023.

(51) Int. Cl.
*A61B 17/00* (2006.01)
*A61M 25/09* (2006.01)

(52) U.S. Cl.
CPC *A61B 17/0057* (2013.01); *A61B 2017/00654* (2013.01); *A61B 2017/00659* (2013.01); *A61B 2017/00778* (2013.01); *A61M 25/09* (2013.01)

(58) Field of Classification Search
CPC ...... A61B 17/0057; A61B 2017/00659; A61B 2017/00623; A61B 2017/00606; A61B 2017/0061; A61B 2017/00615
See application file for complete search history.

(56) References Cited

U.S. PATENT DOCUMENTS

| | | |
|---|---|---|
| 5,810,884 A | 9/1998 | Kim |
| 11,364,024 B2 | 6/2022 | Walters et al. |

(Continued)

FOREIGN PATENT DOCUMENTS

| | | |
|---|---|---|
| EP | 1269919 A1 | 1/2003 |
| WO | 9831286 A1 | 7/1998 |

(Continued)

OTHER PUBLICATIONS

International Search Report and Written Opinion dated Oct. 7, 2024 in connection with International Patent Application No. PCT/US2024/041372, 12 pages.

(Continued)

*Primary Examiner* — Katherine H Schwiker
(74) *Attorney, Agent, or Firm* — Dorsey & Whitney LLP

(57) ABSTRACT

A vascular closure device is configured to seal a puncture in an artery or vein. The vascular closure device includes a deployment assembly having a proximal end and a distal end opposite the proximal end, a suture carried by the deployment assembly, and a footplate carried by the deployment assembly and coupled to the suture. The footplate is configured to exit the distal end of the deployment assembly for deployment in the puncture. The vascular closure device includes a retraction assembly coupled to the footplate, the retraction assembly configured to, after deployment of the footplate, retract the footplate in a proximal direction.

16 Claims, 15 Drawing Sheets

(56)                    References Cited

U.S. PATENT DOCUMENTS

| 2002/0006429 A1 | 1/2002 | Redmond et al. |
| 2009/0069844 A1 | 3/2009 | Green et al. |
| 2011/0077683 A1 | 3/2011 | Huss |
| 2011/0301638 A1 | 12/2011 | Walters |
| 2012/0143243 A1 | 6/2012 | Hill et al. |
| 2014/0052171 A1 | 2/2014 | Tegels |
| 2016/0374655 A1* | 12/2016 | Walters .............. A61B 17/0057 |
| | | 606/217 |
| 2018/0325505 A1* | 11/2018 | Phillips .............. A61B 17/0057 |

FOREIGN PATENT DOCUMENTS

| WO | 2016073870 A1 | 5/2016 |
| WO | 2019168593 A1 | 9/2019 |

OTHER PUBLICATIONS

International Search Report and Written Opinion dated Oct. 8, 2024 in connection with International Patent Application No. PCT/US2024/041373, 12 pages.
"Shaft", Apr. 22, 2009, Merriam-Webster, p. 1 (Year: 2009).
"Wire", Apr. 24, 2016, Dictionary.com, p. 1 (Year: 2016).

\* cited by examiner

VASCULAR CLOSURE DEVICE WITH RETRACTION ASSEMBLY FOR REPOSITIONING A FOOTPLATE

CROSS-REFERENCE TO RELATED APPLICATIONS

The present application claims the benefit of priority under 35 U.S.C. § 119 (c) to U.S. Provisional Appln. Ser. No. 63/517,979, filed Aug. 7, 2023, which is incorporated herein by reference in its entirety.

TECHNICAL FIELD

The present application is directed to a vascular closure device with a retraction assembly for repositioning a footplate.

BACKGROUND

Percutaneous access of the vascular system for vascular device delivery is a common medical procedure. Typically, this involves using a hollow needle to puncture a vessel, then introducing an introducer sheath to open the puncture site for the introduction of catheters and wire guides for navigation through the vascular system to facilitate delivery. For example, in many cases, vascular access requires introduction of catheters and wire guides through the femoral artery. Once the procedure is completed, the devices are removed from the patient and pressure is applied to the puncture site to stop the bleeding. Thereafter, the puncture may be sealed using a closure device.

Closure devices generally consist of three basic sealing components: a footplate (or anchor) member, a sealing member (or plug), and a filament (or suture). To lock the components together within the puncture, a locking member may be used.

SUMMARY

An embodiment of the present disclosure includes a vascular closure device configured to seal a puncture in an artery or vein. Examples of the vascular closure device may include a deployment assembly having a proximal end and a distal end opposite the proximal end, a suture carried by the deployment assembly, and a footplate carried by the deployment assembly and coupled to the suture. The footplate may be configured to exit the distal end of the deployment assembly for deployment in the puncture. The vascular closure device may include a retraction assembly coupled to the footplate, the retraction assembly configured to, after deployment of the footplate, retract the footplate in a proximal direction.

In some embodiments, a vascular closure device may include a deployment assembly having a proximal end and a distal end opposite the proximal end, a suture carried by the deployment assembly, and a footplate carried by the deployment assembly and coupled to the suture. The footplate may be configured to exit the deployment assembly for deployment in the puncture. The vascular closure device may include a tether coupled to the footplate. The tether may be configured to, after the footplate exits the deployment assembly, retract the footplate in a proximal direction, for example in response to manual engagement by a user.

In some embodiments, a vascular closure device may include a deployment assembly having a proximal end and a distal end opposite the proximal end, a suture carried by the deployment assembly, and a footplate carried by the deployment assembly and coupled to the suture. The footplate may be configured to 1) exit the deployment assembly for deployment, and 2) retract in a proximal direction after deployment. The vascular closure device may also include a guide member having an elongated body and a footplate engagement member configured to abut the footplate. After deployment of the footplate, abutment of the footplate engagement member against the footplate may cause the footplate to pivot for retraction in the proximal direction.

Embodiments of the present disclosure include methods for sealing a puncture in an artery or vein. Examples of a method may involve inserting a distal end of a disclosed deployment assembly into the puncture of the artery or vein. The method may also involve causing a footplate of a sealing unit to exit out of the distal end of the deployment assembly and into a lumen of the artery or vein. The method may also involve determining a position of the footplate in the lumen of the artery or vein. The method may also involve retracting the footplate in a proximal direction toward the distal end of the deployment assembly and out of the lumen of the artery or vein.

BRIEF DESCRIPTION OF THE DRAWINGS

The foregoing summary, as well as the following detailed description of example embodiments of the disclosure, will be better understood when read in conjunction with the appended drawings, in which there are shown example embodiments for the purposes of illustration. It should be understood, however, that the application is not limited to the precise arrangements and systems shown in the drawings, in which.

DETAILED DESCRIPTION OF ILLUSTRATIVE EMBODIMENTS

Figure 1:
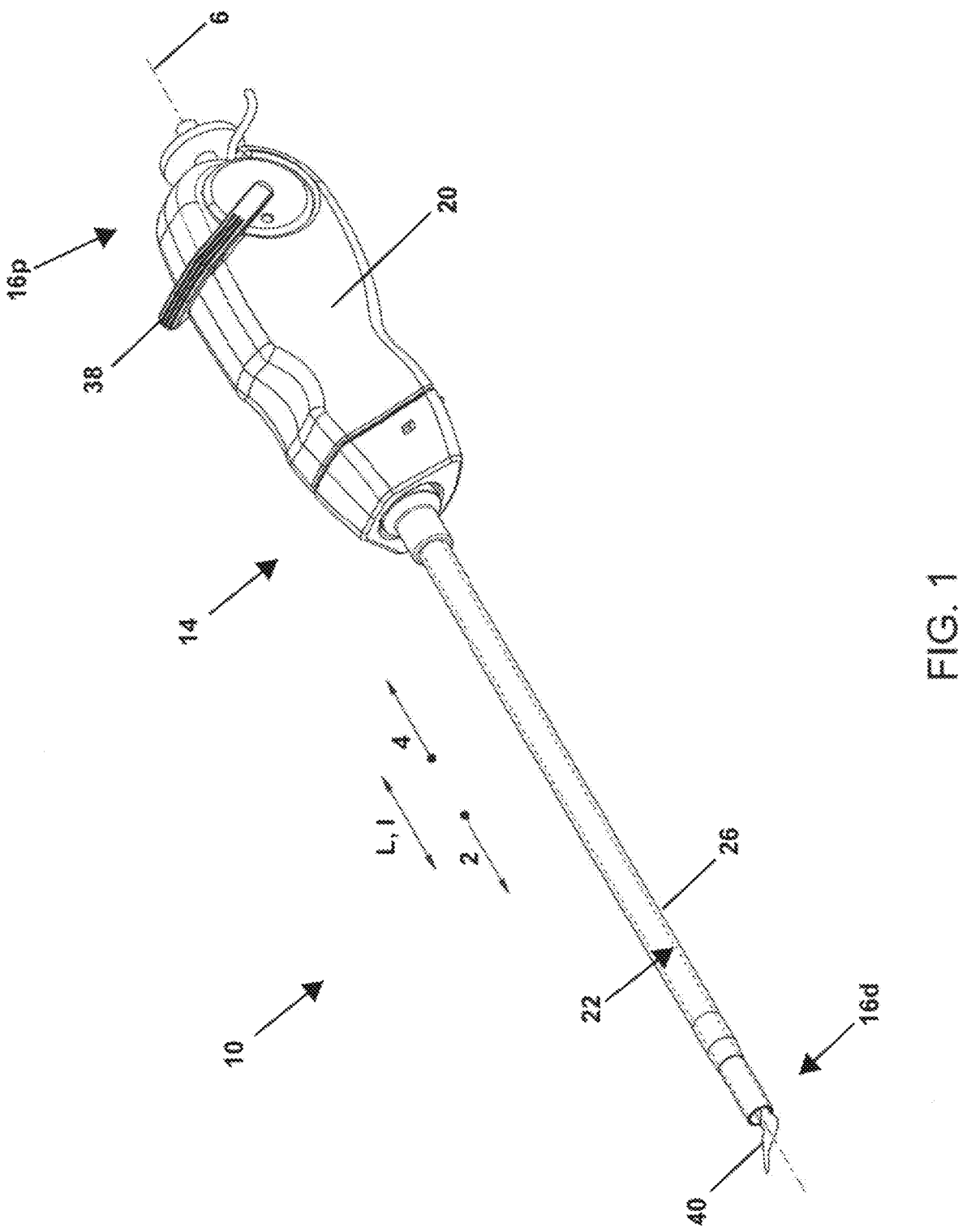
FIG. 1 is a perspective view of a vascular closure device in accordance with an embodiment of the present disclosure.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIG. 1-4, embodiments of a vascular closure device 10 may include a sealing unit 18 at least partially disposed within a deployment assembly 14, and a retraction assembly 50. The vascular closure device 10 can be configured such that after the deployment assembly 14 is inserted into a vessel through a puncture site of the vessel, the sealing unit 18 may be deployed to thereby seal or otherwise close the puncture site of the vessel. After deployment but before the sealing unit 18 is in its final sealing configuration, a user can retract a footplate 40 of the sealing unit 18 in a proximal direction with the retraction assembly 50. The retraction assembly 50, in particular, may allow the user to withdraw or pull back the footplate 40 in the event of incorrect positioning or placement of the footplate 40. Furthermore, the retraction assembly 50 may also provide for the ability to bail out of a deployment procedure and remove the footplate 40 altogether from the puncture site during use.

The deployment assembly 14 may be configured to control the orientation of a footplate 40 of the sealing unit 18 during use. In accordance with the illustrated embodiment, the deployment assembly 14 includes a release component 22 (shown in dashed lines in FIGS. 1 and 2) that restrains the footplate 40, a delivery component 26 that contains at least a portion of the footplate 40 and a suture 44 of the sealing unit 18, and one or more actuators, such as deployment actuator 38. The release component 22 may be operatively coupled or associated with the suture 44 such that actuation of the deployment actuator 38 may cause the release component 22 to 1) release the footplate 40, and 2) apply tension to the suture 44, which urges the footplate 40 against the delivery component 26 and orients the footplate 40 in the sealing position.

Figure 3:
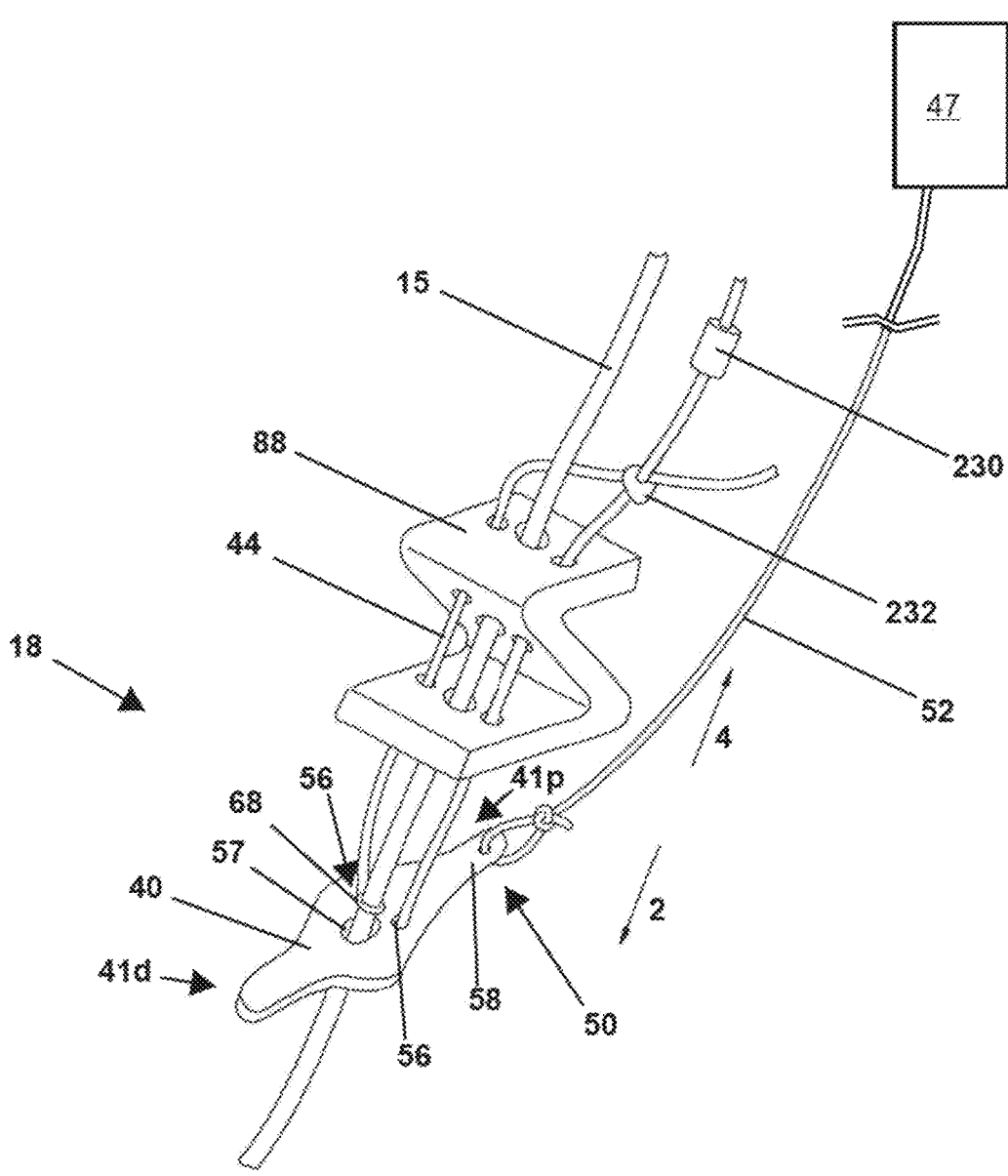
FIG. 3 is a perspective view of a sealing device associated with the vascular closure device shown in FIG. 1.

Turning to FIG. 3, the sealing unit 18 may include the footplate 40 connected to the suture 44, a plug 88 coupled to the suture 44 and spaced from the footplate 40 in a proximal direction 4, and a locking member 230 on the suture 44 and proximal to the plug 88.

Figure 4:
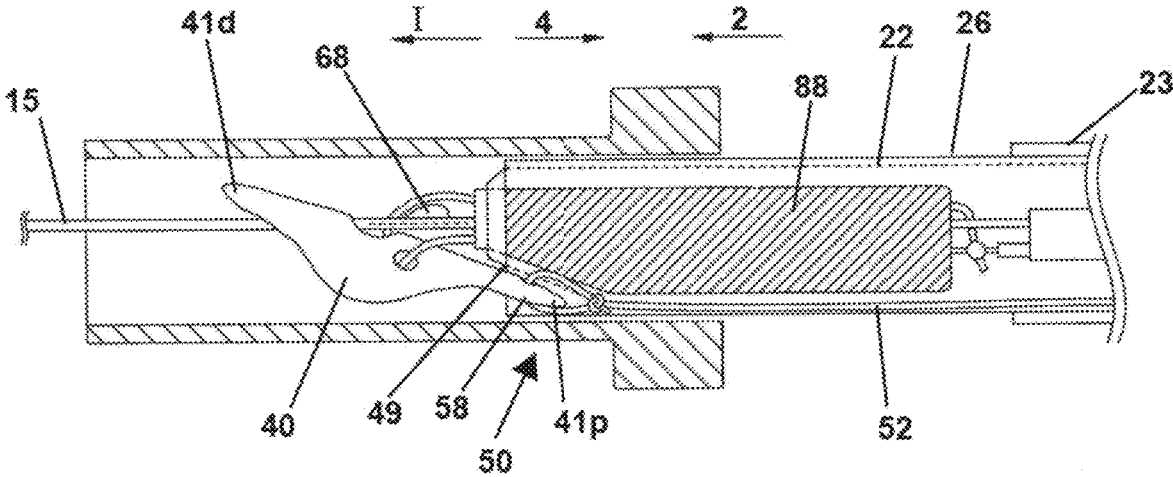
FIG. 4 is a partial sectional view showing the sealing device shown in FIG. 3 disposed in a distal end of the vascular closure device shown in FIG. 1.

The footplate 40 may include or define a distal end 41d and a proximal end 41p opposed to the distal end 41d, a first set of apertures 56 configured to accommodate the suture 44, a guide member aperture 57, and an engagement member, portion, or feature 58. The suture 44 may extend through the first set of apertures 56, as illustrated, such that an end of the suture 44 may be formed into a slidable knot 232. The knot 232 may be slidable along the suture 44 between the plug 88 and the locking member 230. A guide member 15 may extend through the aperture 57. In an implanted state, the footplate 40 may be positioned adjacent to an inner surface of the vessel, and the locking member 230 may squeeze the footplate 40 and the plug 88 against the outer surface of the vessel to seal the puncture. The guide member 15 may extend through the sealing unit 18 and may be configured to receive a guidewire 150, as will be discussed below. The retraction assembly 50 may be coupled to the footplate 40 via the engagement member 58. As shown in FIG. 4, the engagement member 58 in one example may be or may comprise an aperture, through which a tether 52 may be knotted to the footplate 40.

The sealing unit 18 may be formed with materials suitable for surgical procedures. For instance, the footplate 40 can be made of any biocompatible material, non-limiting examples of which may include or comprise a polylactic-coglycolic acid or other synthetic absorbable polymer that degrades in the presence of water into naturally occurring metabolites. In some embodiments, the footplate can be made of stainless steel, biocorrodible iron, and/or biocorrodible magnesium. It should be appreciated, however, that the footplate 40 can be made of other materials and can have other configurations so long as it can be seated inside the vessel against the vessel wall.

The plug 88 can comprise a strip of compressible, resorbable, collagen foam and can be made of a fibrous collagen mix of insoluble and soluble collagen that may be crosslinked for strength. It should be appreciated, however, that the sealing plug 88 can have any configuration as desired and can be made from any material as desired. The suture 44 can be any elongate member, such as, for example a filament, thread, or braid.

The deployment assembly 14, including the release component 22 and delivery component 26, may be constructed and may function in accordance with the devices, systems, and methods disclosed in U.S. Pat. No. 11,364,024, the entire contents of which are incorporated by reference into the present application. Referring again to FIGS. 1, 2, and 4, the deployment assembly 14 may be elongate along a longitudinal direction L and may include a proximal end 16p and a distal end 16d spaced from the proximal end 16p along an axis 6 that is aligned with the longitudinal direction L. The longitudinal direction L can include and define a distal direction 2 that extends from the proximal end 16p toward the distal end 16d. Further, the longitudinal direction L can include and define a proximal direction 4 that is opposite the distal direction 2 and that extends from distal end 16d toward the proximal end 16p. The deployment assembly 14 may be configured to insert the footplate 40 into the vessel along an insertion direction I (see FIG. 4). The longitudinal direction L can be aligned with the insertion direction I during a portion of the sealing procedure.

Figure 2:
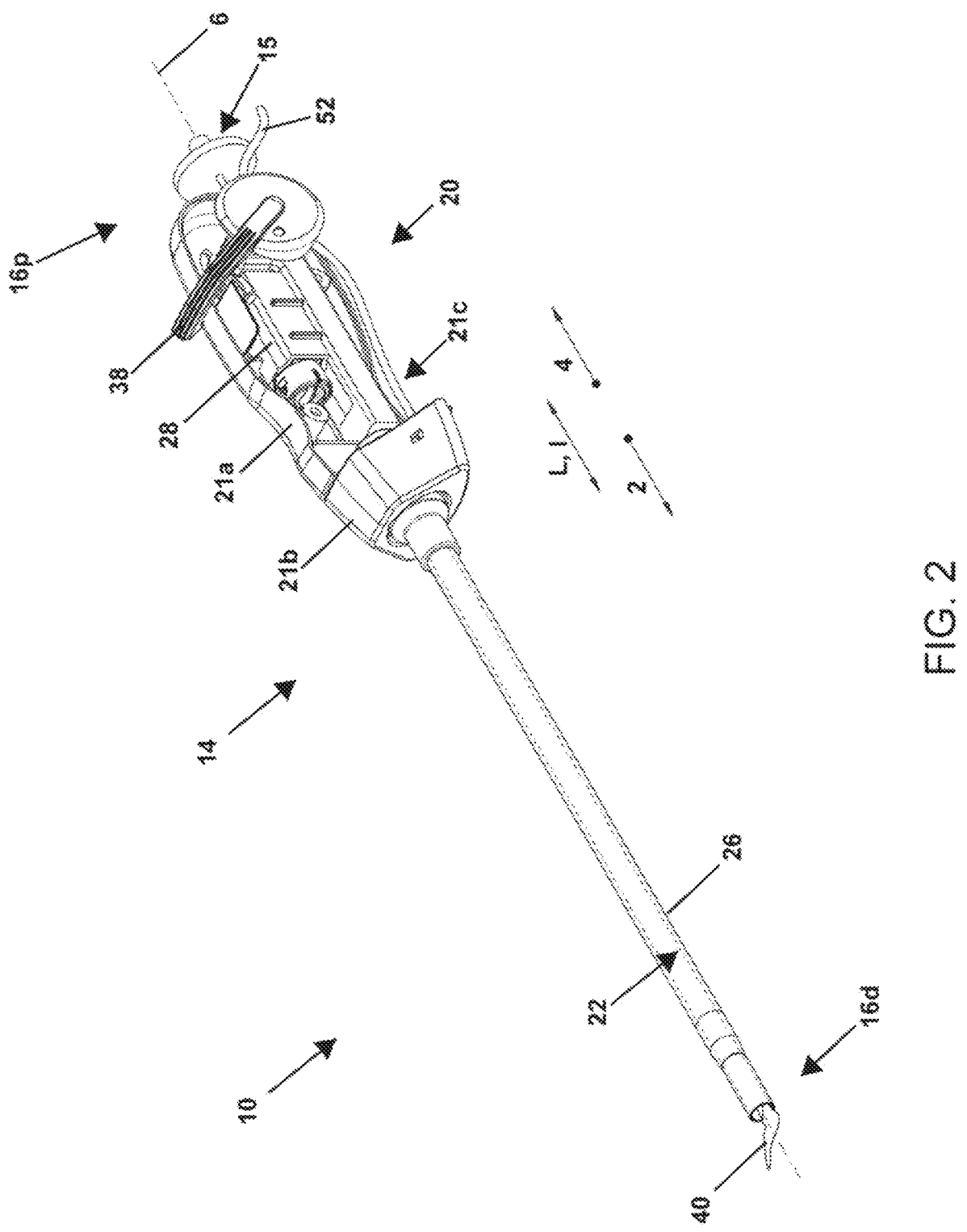
FIG. 2 is a partial cut-away view of the vascular closure device shown in FIG. 1.

Turning to FIGS. 1 and 2, in accordance with the illustrated embodiment, the deployment assembly 14 may include a handle member 20, the release component 22 supported by the handle member 20, the delivery component 26, a tensioner 28 supported by the handle member 20, and at least one deployment actuator 38. A portion of release component 22 is shown in dashed lines in FIGS. 1 and 2.

The deployment actuator 38 may be coupled to both the handle member 20 and the release component 22. The deployment actuator 38 may be configured to 1) cause the release component 22 to move in the proximal direction 4 from a first or initial position relative to the delivery component 26 into a second or releasing position relative to the delivery component 26, and 2) apply a tensile force to the suture 44 during or subsequent to movement of the release component 22 from the initial position into the release position. The description below refers to the release component 22 being movable relative to the delivery component 26, but the deployment assembly 14 can be configured so that the delivery component 26 is movable relative to the release component 22. The deployment assembly 14 may also include the guide member 15 that extends through the deployment assembly 14, and an optional outer sheath 23 (see FIG. 4) that contains and supports portions of the release component 22 and delivery component 26.

Continuing with FIGS. 1 and 2, the handle member 20 may include a housing 21*a*, a sheath hub 21*b* and a cavity 21*c* defined at least partly by housing 21*a* and sheath hub 21*b*. The cavity 21*c* may be sized to contain a portion of the release and delivery components 22 and 26 and the tensioner 28. The sheath hub 21*b* may be configured to mate with an access sheath 208 (see FIG. 6).

Turning to FIGS. 1 and 2, the release component 22 may be elongate along a first or longitudinal direction L and may define a distal end and a proximal end spaced from the distal end along the longitudinal direction L. The release component 22 may include a release tube body that is elongate along the longitudinal direction L. The release tube body may define a release tube channel that extends along the longitudinal direction L from the hub toward the proximal end. The release tube channel may be sized to slidably receive a portion of the delivery component 26 such that the release component 22 is movable relative to the delivery component 26. Embodiments of one or more of these features, including additional features of the release component 22, are described in U.S. Pat. No. 11,364,024.

The tensioner 28 may be positioned in the handle member 20 and coupled to the proximal end of the release component 22. In one example, the suture 44 may extend around a pulley and into the tensioner 28. As the release component 22 is pulled in the proximal direction 4, the pulley may pull the suture 44 in proximal direction 4, thereby applying a tensile force to the footplate 40. Other arrangements may be used to apply to tension to the suture 44 and footplate 40 as needed.

As shown in FIGS. 2-4, the delivery component 26 may be coupled to the tensioner 28 and may extend along the release component 22 toward the distal end 16*d* of the deployment assembly 14. The delivery component 26 may include a delivery tube body that is elongate along the first direction L and that defines a distal end and a proximal end spaced from the distal end in the first direction L. The delivery tube body may define a delivery tube channel that extends at least partially through the delivery tube body along the first direction L. As illustrated, the proximal end of delivery component may be fixed to the tensioner 28, and the distal end of delivery component may be configured to hold at least a portion of the sealing unit 18 (see FIG. 4). Embodiments of one or more of these features, including additional features of the release component 26, are described in U.S. Pat. No. 11,364,024.

The delivery tube channel may be sized to retain at least a portion of the sealing unit 18. In particular, the plug 88 and locking member 230 may be retained within the delivery tube channel, while the footplate 40 may be configured to be initially trapped between the delivery component 26 and the release component 22. For instance, the distal end of the release tube may define an offset surface 49, which can be angled with respect to the longitudinal axis 6. The offset surface 49 and inner surface of the delivery component may define a cavity that receives the proximal end 41*p* of the footplate 40 when release component 22 is in the initial position (as shown in FIG. 4). The angle of the offset surface 49 can define the orientation of the footplate 40 in this initial position, whereby the distal end 41*d* of the footplate 40 is spaced some distance in the distal direction 2 beyond the distal ends of the release and delivery components 22 and 26, respectively. The suture 44 may extend from the footplate 40 through the delivery tube channel, through the proximal end around the pulley of the tensioner 28. The guide member 15 may extend through the delivery component and may exit the distal end 16*d* of the vascular closure device 10.

When the deployment actuator 38 is actuated, the release component 22 may move in the proximal direction 4, thereby releasing the proximal end 41*p* of the footplate 40 from between the release component 22 and the delivery component 26. As the release component 22 moves in the proximal direction 4, the suture 44 will be pulled in the proximal direction 4 to thereby place the suture 44 in tension and urge the footplate 40 against the distal end of the delivery component 26. At this point, the footplate 40 may be oriented in the sealing position (see FIGS. 11 and 12, for example). In the scaling position, the footplate 40 has been repositioned so that the footplate 40 is placed against the distal end of the delivery component 26 and is oriented more transversely with respect to the axis 6 compared to the position when the footplate 40 is restrained by the release component 22.

The deployment assembly 14 can include one or more actuators that are configured to transition the release component 22 into a releasing position and to cause a tension to be applied to suture 44 when footplate 40 is released from the release component 22, as described above. The deployment actuator 38, for instance, may engage the release component 22 such that motion of the deployment actuator 38 relative to the handle member 20 may cause the release component 22 to translate in the proximal direction 4 and further apply a tension to the suture 44. The result may be that rotation or movement of the deployment actuator 38 causes the release component 22 to translate in the longitudinal direction L. As shown in the drawings, the deployment actuator 38 can be configured as a lever that is rotatably coupled to the handle member 20. The deployment actuator 38, however, can be a knob or a slide. It should be appreciated, however, that the deployment actuator 38 can have other configurations as desired and is not limited to the disclosed lever.

The retraction assembly 50 may be configured to retract the footplate 40 in a proximal direction. The retraction assembly 50 may include a tether 52 coupled to the footplate 40 and the guide member 15 engaged with the footplate 40.

The tether 52 may be or comprise any elongated element coupled to the footplate 40. As such, the tether may be an elongated shaft, suture, filament, wire, or rod. In some examples, the tether 52 may resemble a rip cord in form and/or function, such that pulling the tether 52 proximally may abort, in effect, the deployment of a sealing unit 18 in the event one or more components of which, such as footplate 40, are improperly positioned. In the embodiment shown, the tether 52 extends through the deployment assembly 14. However, in some configurations, the tether may extend alongside the deployment assembly 14. The retraction assembly may also include a retraction actuator 47 configured to pull the tether 52 in a proximal direction in order to retract at least the footplate 40 in a proximal direction that is opposite a distal direction. In one example, the actuator 47 may be a push-pull member, which may include a rod and wire. In another example, the actuator 47 may be a rotatable knob, rotatable lever, or a slide. Proximal pulling of the tether 52, and thus footplate 40, may be prompted by a user in response to a determination that the footplate is not positioned correctly in or near an inner vessel wall. In this manner, the tether 52 may provide a bailout mechanism for retracting the footplate during a procedure.

Figure 5:
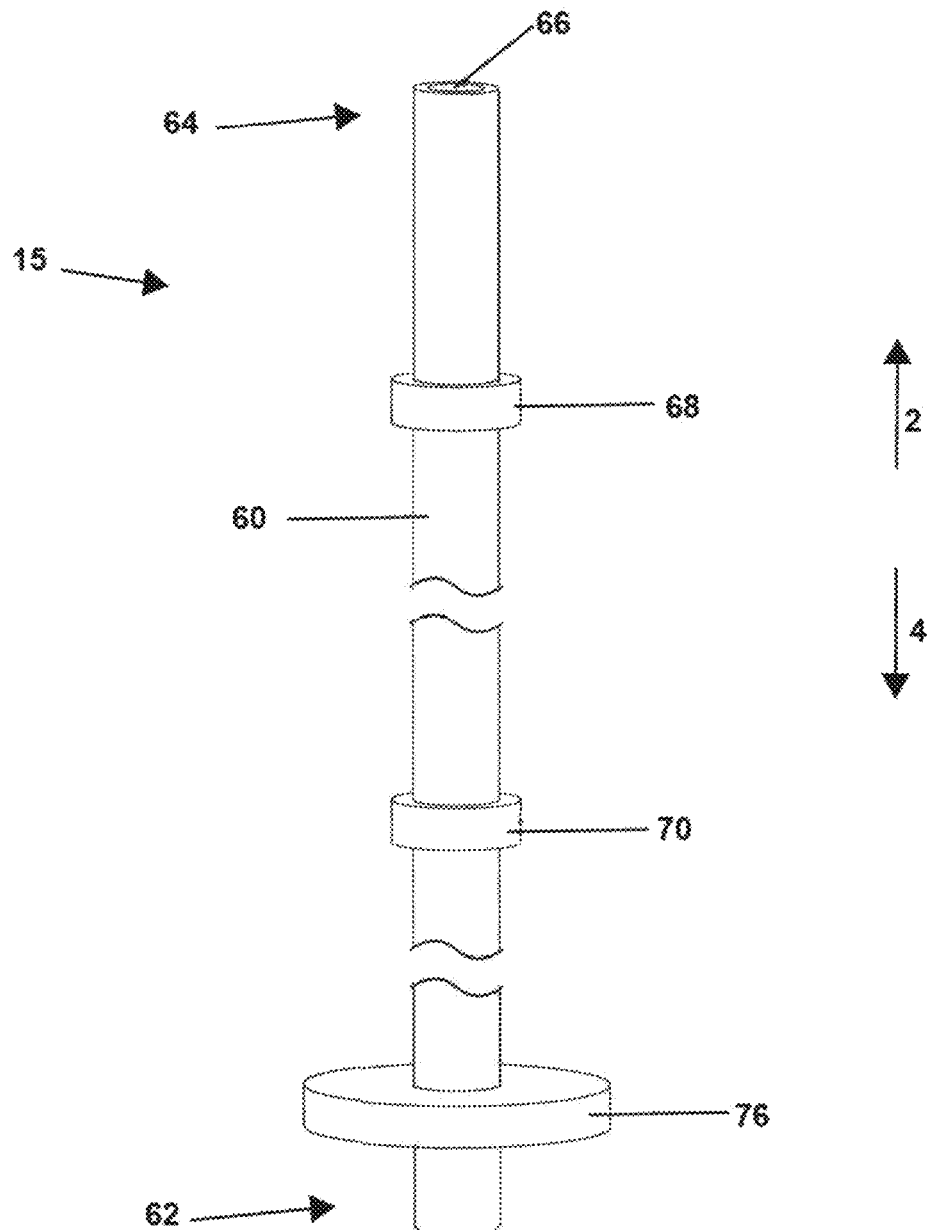
FIG. 5 is a perspective view a guide member and grip portion for the vascular closure device shown in FIG. 1.

As shown in FIG. 5, the guide member 15 may have an elongate body 60 having proximal end 62, a distal end 64, and a lumen 66 that extends from the proximal end 62 to the distal end 64. The lumen 66 is configured to receive a guidewire therethrough, such as guidewire 150 (see FIGS. 6-10). The guide member 15 may also include footplate engagement member 68 configured to abut the footplate 40. The guide member 15 may also include an advancement engagement member 70 configured to, when a force is applied to the advancement engagement member 70, advance the guide member 15 in the distal direction. The guide member 15 may also include an actuator 76, which may be configured as a grip member, which in some examples may be manually engageable by a user.

After deployment of the footplate 40, abutment of the footplate engagement member 68 against the footplate 40 may cause the footplate 40 to pivot for retraction in the proximal direction. More specifically, retraction of the tether 52 and advancement of the guide member 15 in a distal direction until the footplate engagement member 68 abuts the proximal surface of the footplate 44 may cause the footplate 40 to pivot for retraction in a proximal direction.

In operation, the deployment assembly 14 may be initially configured to insert the footplate 40 into the vessel. When the deployment actuator 38 is actuated, the release component 22 may move in the proximal direction 4 relative to the delivery component 26 into the releasing position, thereby releasing the proximal end 41p of the footplate 40 from between the release component 22 and the delivery component 26. As the release component 22 moves in the proximal direction 4, the suture 44 may be pulled in the proximal direction 4 to thereby place the suture 44 in tension and urge the footplate 40 against the distal end of the delivery component 26. At this point, the footplate 40 may be oriented in the sealing position (see FIGS. 11 and 12, for example). Accordingly, the release component 22 may be configured to restrain the footplate 40 of the sealing unit 18 during insertion of the vascular closure device 10 into the vessel and subsequently release the footplate 40 so that the footplate 40 can be oriented for the sealing procedure.

In certain cases, the user may need to reposition the footplate 40. In this situation, the user can determine a position of the footplate 40 in the lumen of the artery or vein using typical visualization procedures, such a puncture locators, radiography, or other means to identify the location of the footplate. The user can retract the footplate 40 in a proximal direction toward the distal end of the deployment assembly and out of the lumen of the artery or vein. In this instance, retracting the footplate 40 in the proximal direction may further comprise retracting a tether (e.g., tether 52) coupled to the footplate. In addition, the user can advance the footplate engagement member 68 of a guide member (e.g., guide member 15) against a proximal surface of the footplate 40, thereby causing the footplate 40 to pivot for retraction in the proximal direction. The footplate can be retracted back toward or into the delivery assembly. In certain instances, the user may cause the plug 88 to exit out of the deployment assembly and then cause retraction of the sealing plug 88 back toward the distal end of the deployment assembly. In any event, after retracting the footplate 40 in the proximal direction, the user can readvance the footplate 40 in the distal direction toward the lumen of the artery or vein into the correct position.

Embodiments of the present technology will now be described with respect to exemplary large bore procedures that utilize the vascular closure device 10. In order to perform any of the related procedures, the user gains percutaneous access to, for example, the femoral artery, causing a puncture site in the artery. To gain percutaneous access to the artery, the Seldinger technique may be used. For example, a hollow bore needle may be inserted into the artery. A guidewire 150 may then be advanced through the hollow needle and into the femoral artery a sufficient distance to allow removal of the needle without the guidewire 150 pulling out of the vessel. Removing the needle leaves the guidewire 150 in place, with a portion of the guidewire 150 extending into the artery. The guidewire 150, extending from outside the patient into the femoral artery, provides for an entry guide for other medical devices, including the vascular closure device 10. Therefore, once the guidewire 150 is positioned in the vessel of the patient, catheters or introducers of gradually increasing diameters may be advanced over the guidewire 150 and through the puncture into the artery to further open the puncture site. Then, an introducer/procedure access sheath set (i.e. an introducer inside an access tube or sheath) may be moved along the guidewire 150 such that a distal end of the sheath moves into the vessel through the puncture site. Once properly positioned, the introducer can be removed such that the sheath provides for sizable access to the vessel interior from outside the body.

After the relevant procedure is completed, the puncture site in the artery created by the bore needle during percutaneous access of the artery may be closed. The vascular closure device 10 may be used to seal the puncture site. FIGS. 6-16 show schematic views of the vascular closure device 10 during the process of closing a puncture site 200 in a vessel (e.g. artery) wall 204.

Figure 6:
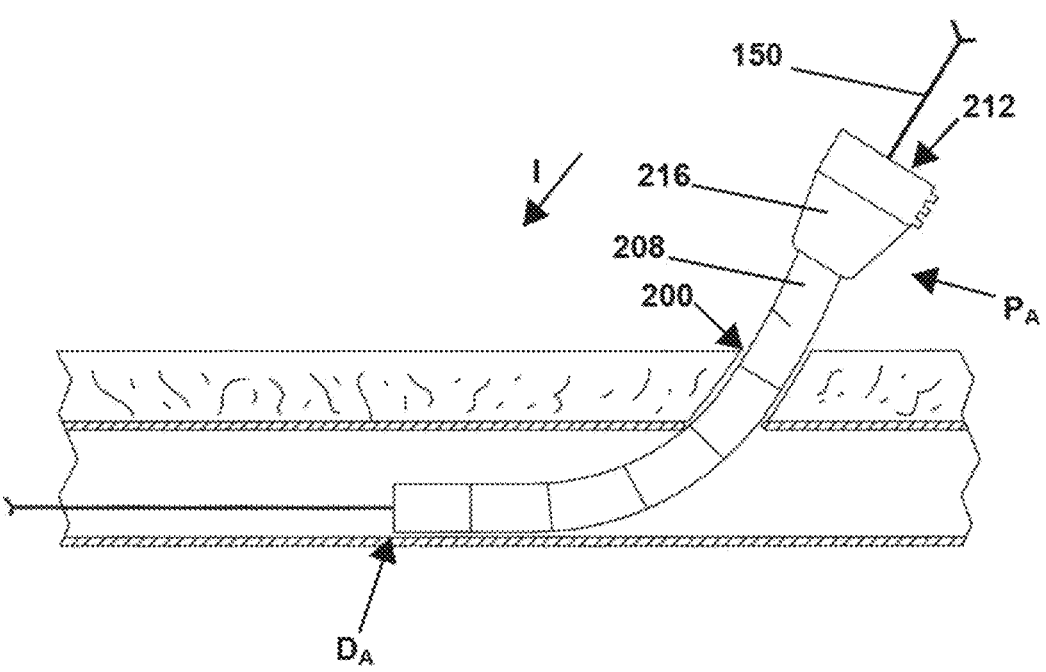
FIG. 6 is a schematic showing an access sheath partially disposed within a vessel through a puncture site in the vessel.

Now in reference to FIG. 6, to deliver the vascular closure device 10 to the puncture site 200 so that the closure device 10 can seal the puncture site 200, the introducer/procedure sheath set or assembly may be replaced with a closure access sheath 208. For example, as shown in FIG. 6, the procedure sheath is exchanged for the closure access sheath 208 by removing the procedure sheath from the patient, leaving the guidewire 150 in place, and subsequently moving the closure access sheath 208 along the guidewire 150 or otherwise positioning the access sheath 208, such that a portion of the access sheath 208 is disposed within the vessel through the puncture site 200. As shown in FIG. 6, the access sheath 208 may define a distal end $D_A$, a proximal end $P_A$, and an internal access channel 212 that extends from the proximal end $P_A$ to the distal end DA along an insertion direction I. The access sheath 208 may further include a sheath hub 216 at its proximal end $P_A$. The sheath hub 216 may be configured to couple to the vascular closure device 10 when the vascular closure device 10 is inserted into the access channel 212 along the insertion direction I.

Figure 7:
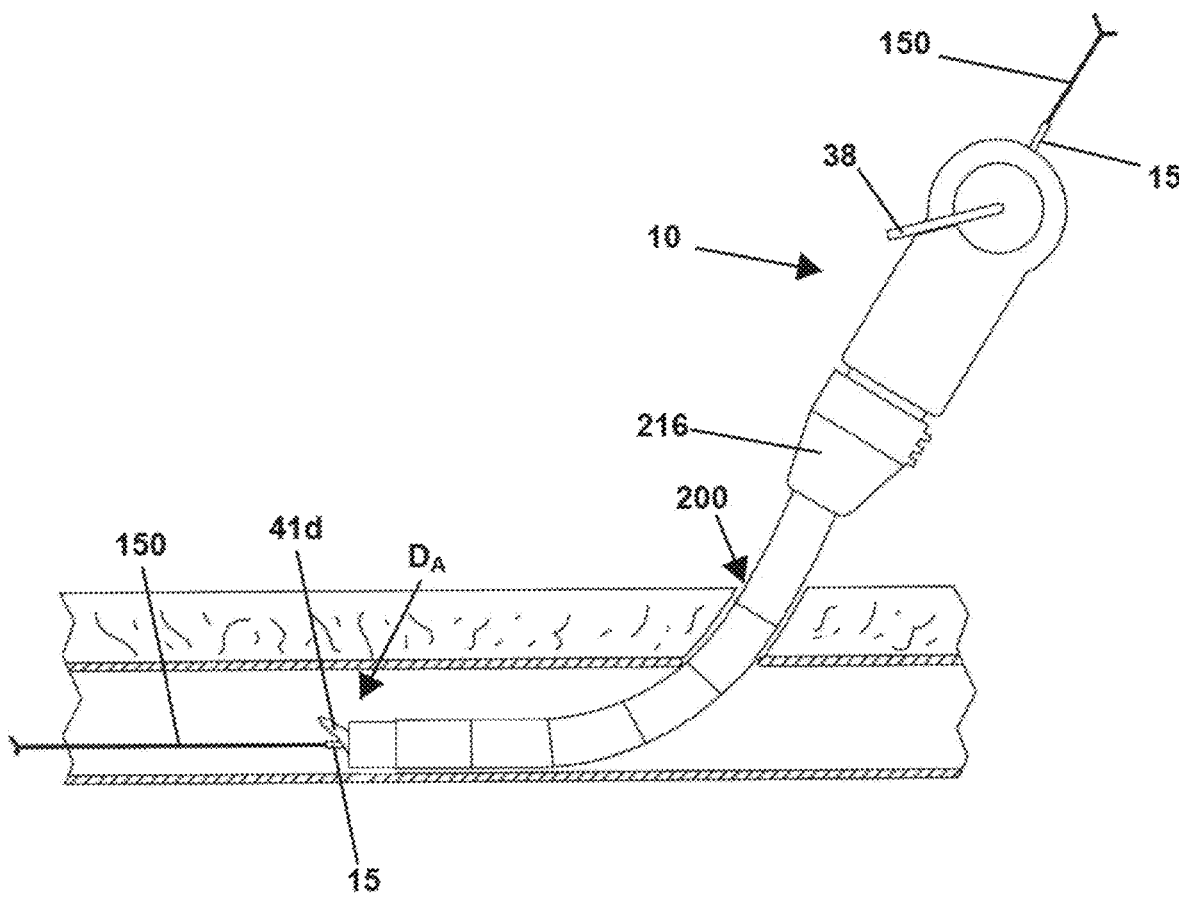
FIG. 7 is a schematic showing the closure device of FIG. 1 translated into an access channel of the access sheath such that a distal end of the footplate is positioned distal to a distal end of the access sheath and over a guidewire.

As shown in FIG. 7, the vascular closure device 10 can be positioned by translating, extending, or otherwise advancing the vascular closure device 10 into and through the access channel 212 along the insertion direction I, such that a portion of the footplate 40 (e.g. distal portion 41d) may protrude from the distal end $D_A$ of the access sheath 208 and into the vessel. Once fully inserted, the vascular closure device 10 can couple to the sheath hub 216. A proximal end of the footplate 40 may be coupled to the release component 22 and the delivery component 26 while the vascular closure device 10 is being moved into the vessel through the puncture site 200 of the vessel. While the proximal end of the footplate 40 is fixed, the footplate 40 may be oriented in a pre-sealing position whereby at least the proximal end of the footplate 40 is concealed and thus prevented from dragging against the vessel wall during positioning of the footplate 40 within the vessel.

Figure 8:
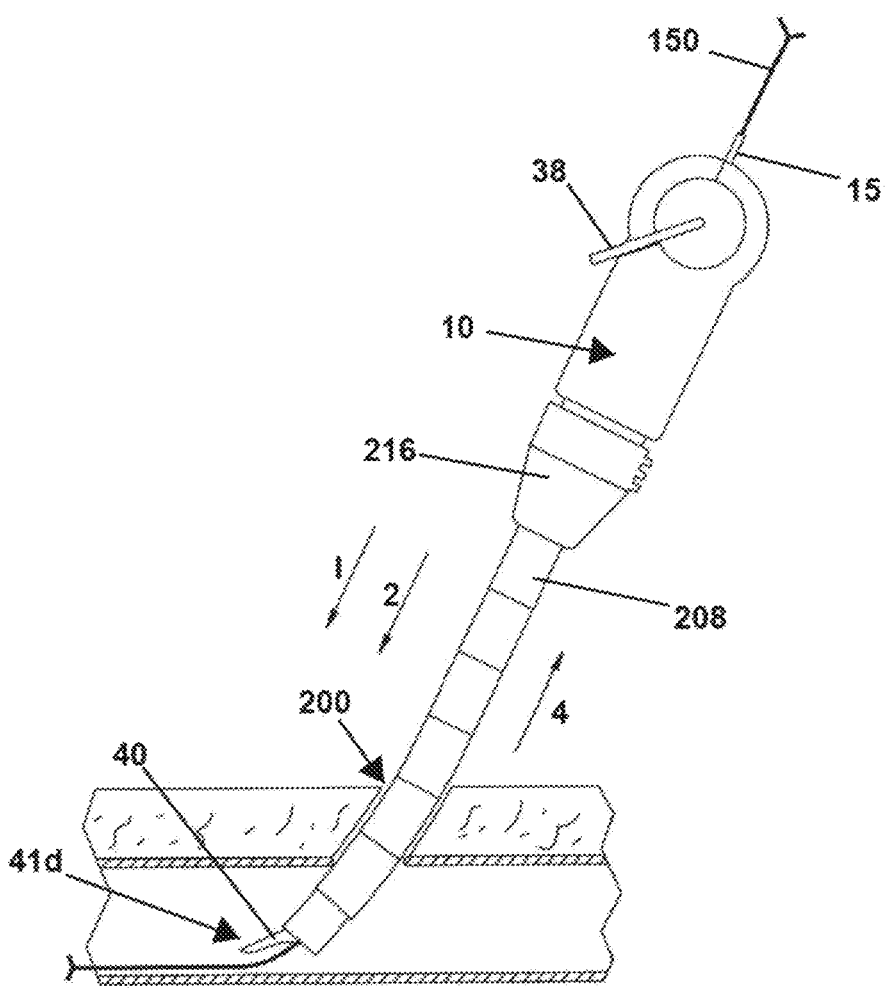
FIG. 8 is a schematic showing positioning of the closure device by pulling in a proximal direction.
Figure 9:
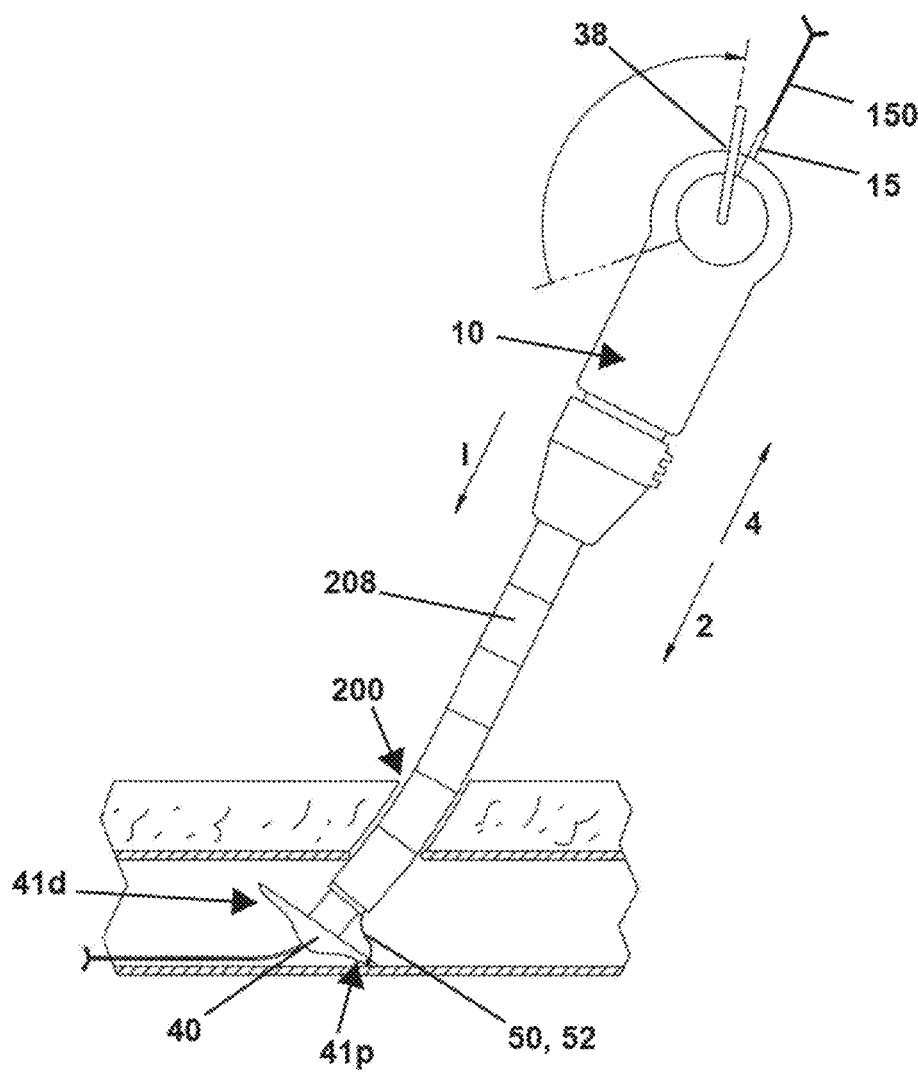
FIG. 9 is a schematic showing actuation of the actuator to release the footplate and apply a tension to a filament.
Figure 10:
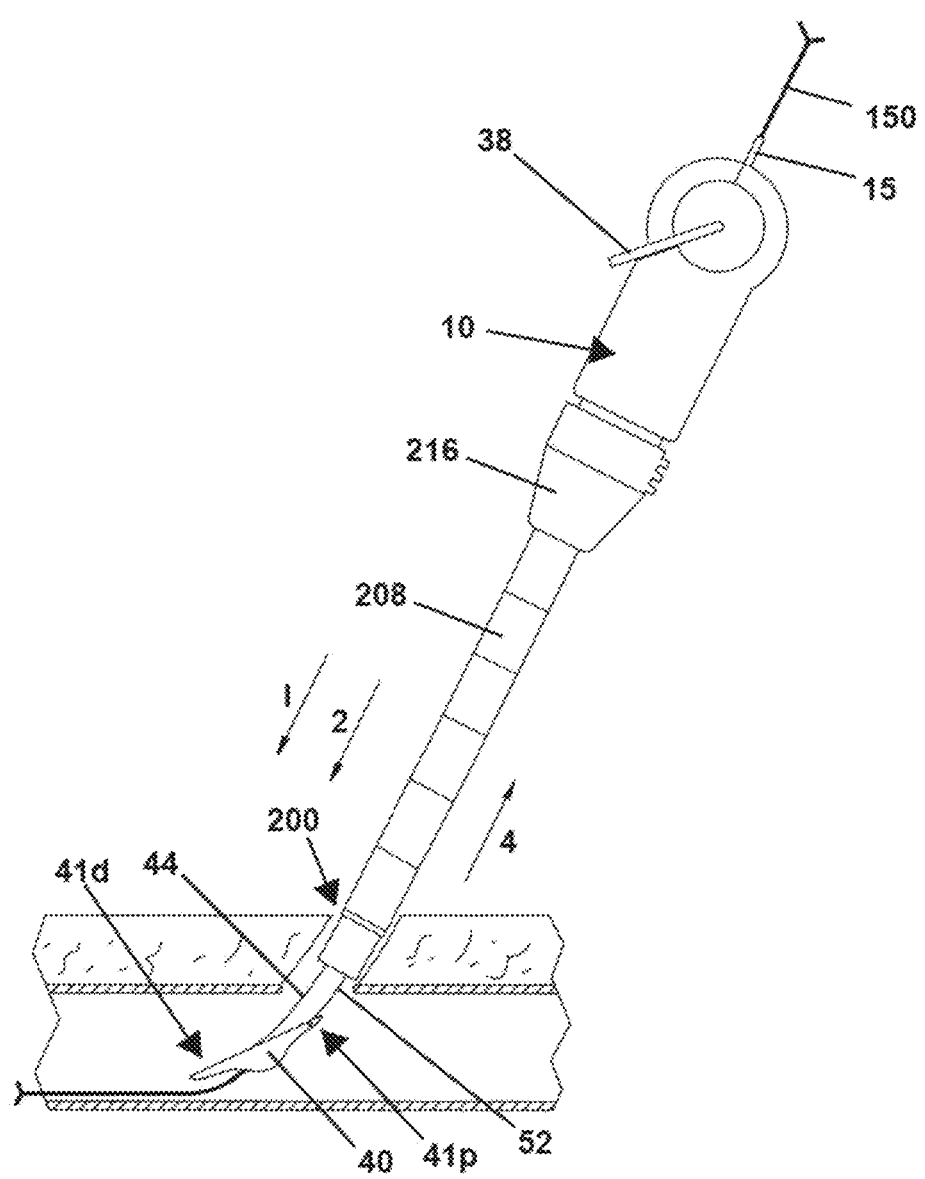
FIG. 10 is a schematic showing a tether retracting the footplate in a proximal direction.

Once the vascular closure device 10 is properly positioned within the access sheath 208, the footplate 40, and in particular, the entire access sheath 208 and vascular closure device 10 combination, can be moved proximally such that the footplate 40 is positioned adjacent to the puncture site 200, as shown in FIGS. 6-8. As noted above, in some cases the footplate 40 may not be in the proper position for sealing after its insertion in a target vessel. In this situation, the user can determine a position of the footplate 40. As shown in FIGS. 9 and 10, the user can retract the footplate 40 in a proximal direction toward the distal end of the deployment assembly 14 and even out of the lumen of the artery or vein in some examples. In this instance, retracting the footplate in the proximal direction further comprises retracting a tether 52 coupled to the footplate 40. In addition, the user can advance the footplate engagement member of a guide member against a proximal surface of the footplate, thereby causing the footplate 40 to pivot for retraction in the proximal direction, as shown in FIG. 10. The footplate 40 can be retracted back toward or into the delivery assembly 10. After retracting the footplate in the proximal direction, the use can readvance the footplate 40 in the distal direction toward the lumen of the artery or vein into the correct position, as shown in the progression from FIGS. 10 to 11.

Figure 11:
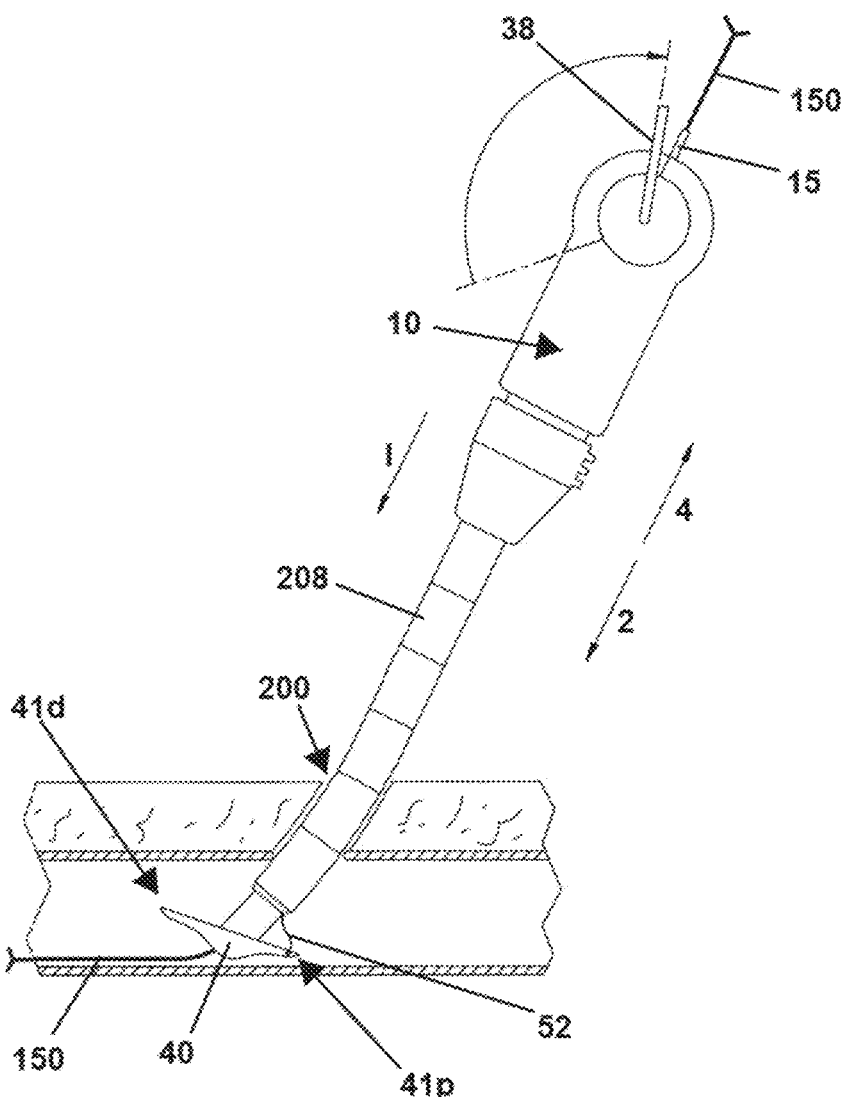
FIG. 11 is a schematic showing release of the footplate following a bailout.

Once the footplate 40 is adjusted to a proper position, the deployment actuator 38 may be actuated to release the footplate 40 from the release tube and subsequently apply a tension to the suture 44 so as to pull the footplate 40 against the distal end of the delivery component 26, as shown in FIG. 11. At this point the footplate 40 may be oriented in a scaling position.

Figure 12:
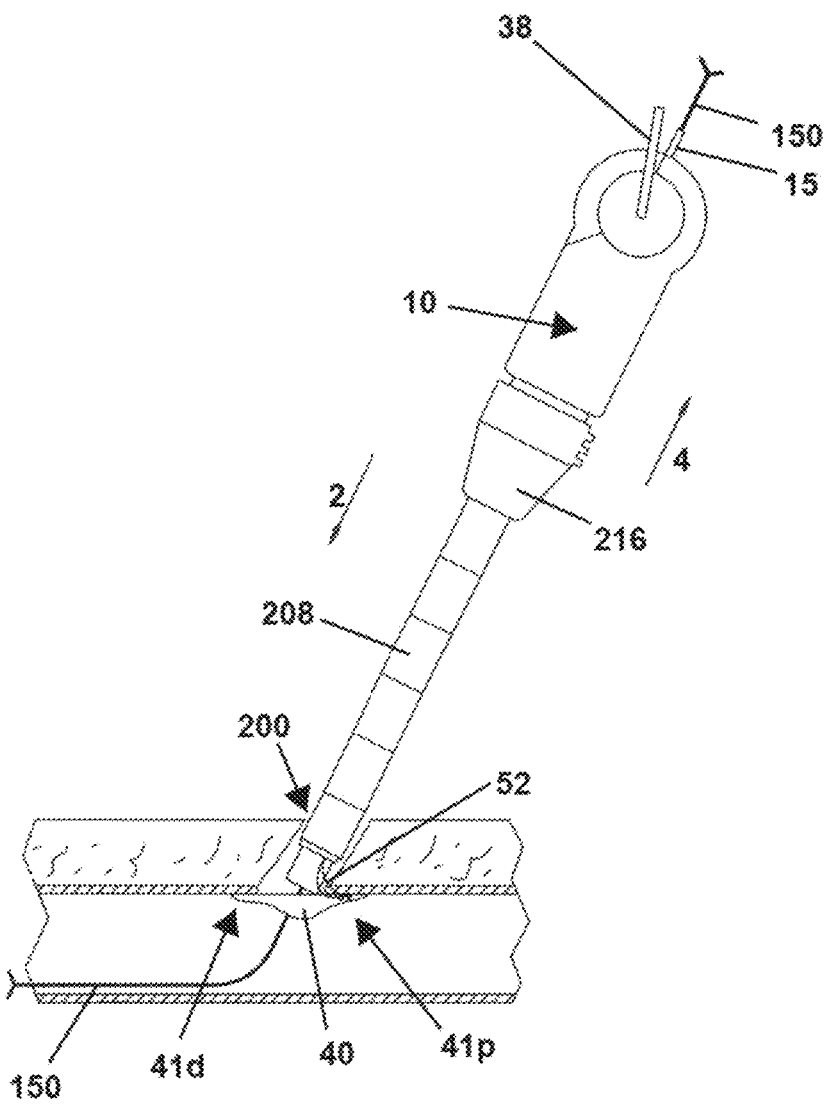
FIG. 12 is a schematic showing the deployment assembly being pulled in a proximal direction such that the footplate abuts the vessel wall.
Figure 13:
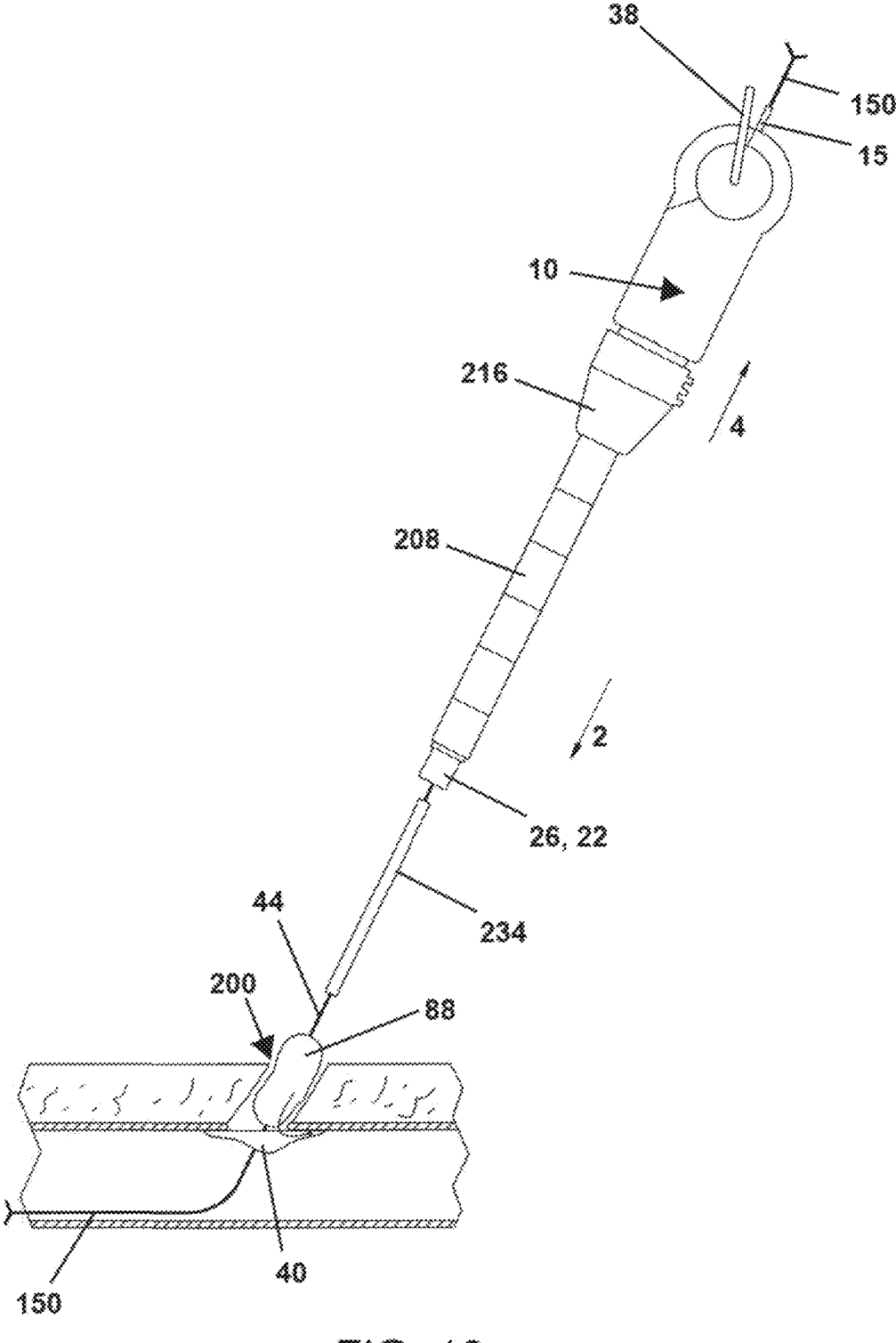
FIG. 13 is a schematic showing deployment of a plug of the closure device.
Figure 14:
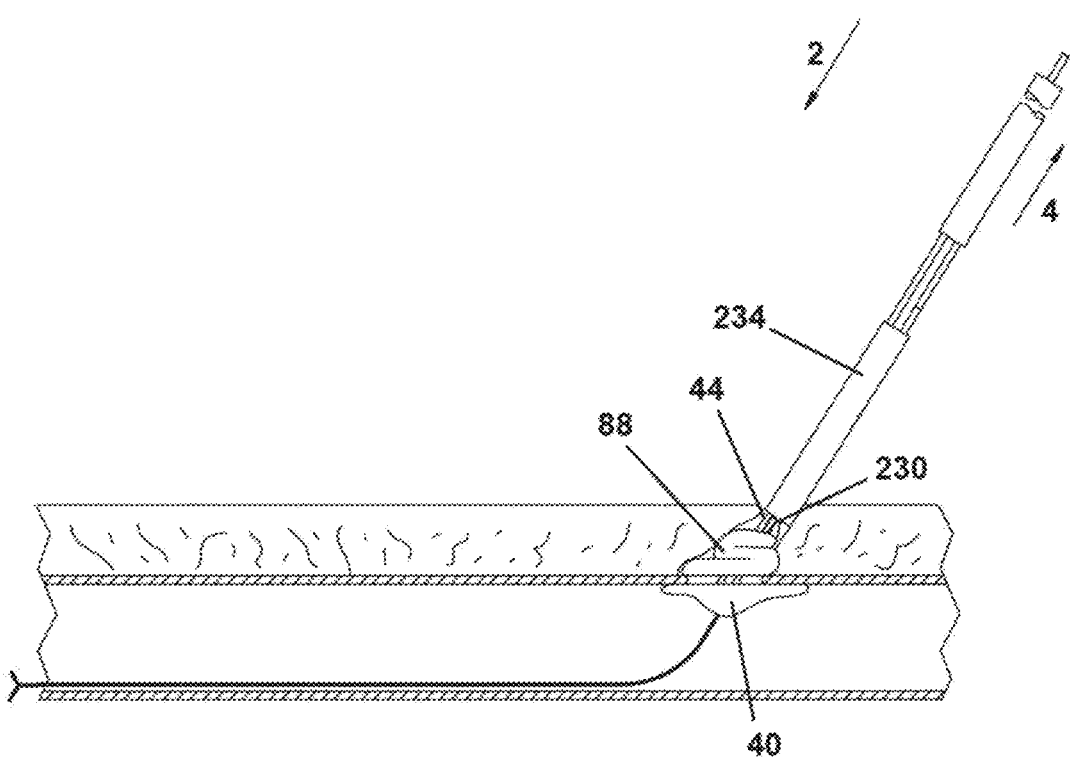
FIG. 14 is a schematic showing deployment of a locking member against the plug.

With the footplate 40 in the sealing position, the deployment assembly 14 along with the access sheath 208 can together be pulled proximally such that the footplate 40 abuts the vessel wall 204, as shown in FIG. 12. As shown in FIG. 13, further pulling of the device 14 and sheath 208 may cause the sealing unit 18, including the footplate 40, plug 88, locking member 230, suture 44, and a tamper 234, to be fully withdrawn from the delivery component 26. By pulling on the suture 44 in a direction away from the vessel (i.e. in a direction opposite the insertion direction I) the suture 44 may be tensioned and the footplate 40 moved fully into position against an inner surface of the vessel wall 204 at the puncture site 200. The tension in the suture 44 may also pull the plug 88 into the puncture site 200, and may cause the plug 88 to substantially fill the puncture site 200, as shown for instance in FIG. 14. After the plug 88 is in contact with blood or other fluids within the puncture site 200, the plug 88 may expand and fill the remainder of the puncture site 200.

Figure 15:
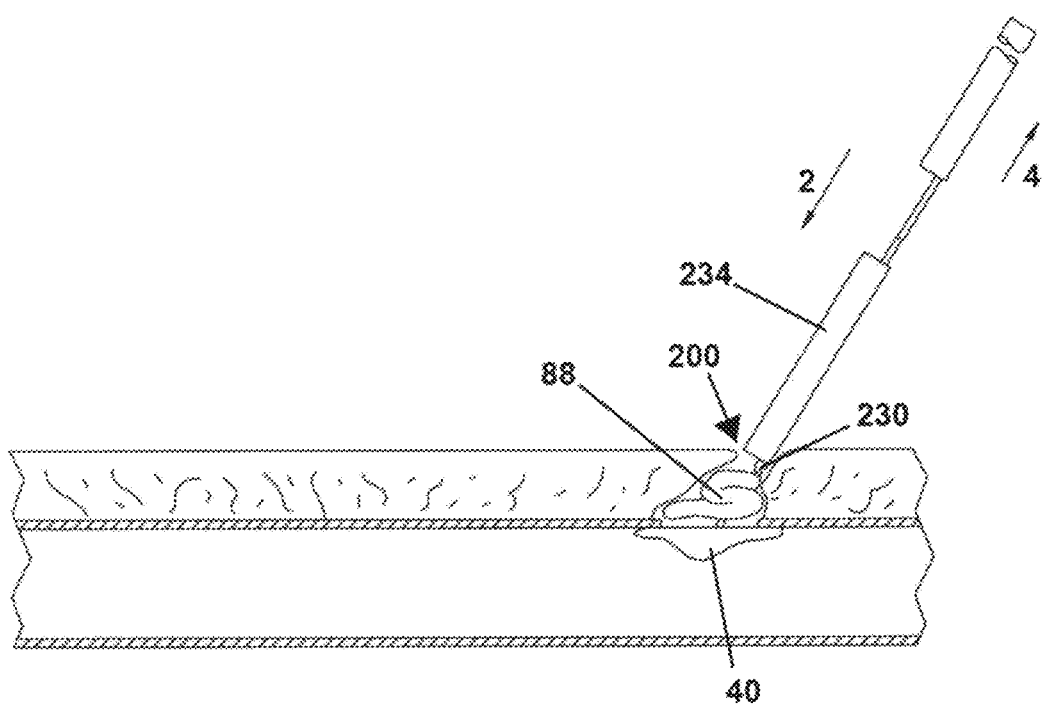
FIG. 15 is a schematic showing the locking member being tamped against the plug with a tamper.

After the user has pulled the suture 44 to cause tension in the suture 44 and to cause the plug 88 to enter the puncture site 200, the user may advance the tamper 234 distally along the guidewire 150 and the suture 44. As shown in FIG. 15, the tamper 234 may contact the locking member 230 and advance the locking member 230 distally along the suture 44 until the locking member 230 contacts the plug 88 and presses the plug 88 against an outer surface of the vessel. As the plug 88 is compressed by the tamper 234 and locking member 230, the plug 88 may fold over the top of and inside the puncture site 200. It should be appreciated, however, that in some embodiments, the delivery component 26 may be pulled such that the plug 88 is removed from the delivery component 26 within the release component 22, and the tamper 234 may be employed within the release component 22. In such an embodiment, the release component 22 may help control the plug 88 as it is being tamped against the puncture site.

Figure 16:
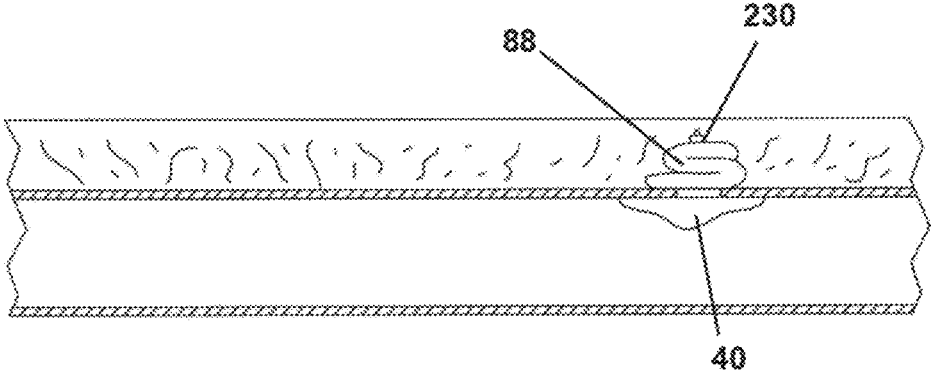
FIG. 16 is a schematic showing the deployment of the sealing device fully sealing the puncture site.

As further shown in FIGS. 15 and 16, the locking member 230, together with the plug 88 and the footplate 40, may effect a seal of the puncture site 200. Tension may be maintained on the suture 44 throughout the deployment of the plug 88 from the delivery component 26. After the puncture site 200 is sealed, the guidewire 150 can be removed as shown in FIG. 15. As the guidewire 150 is removed, the suture 44 may remain in tension, and the user can re-compress the plug 88 with the tamper 234 as desired to confirm a proper seal of the puncture site 200. Once properly sealed, the suture 44 can be cut so that the remaining suture 44, tamper 234, and other components of the sealing unit 18 can be removed from the puncture site 200, as shown in FIG. 16. Remaining portions of the sealing unit 18, including the footplate 40, plug 88, portion of suture 44, and locking member 230 (depending on material used) may resorb into the body of the patient over time.

While the foregoing description and drawings represent the preferred embodiment of the present invention, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the present disclosure may be used with many modifications of structure, arrangement, proportions, materials, and components, which are particularly adapted to specific environments and operative requirements without departing from the principles of the present disclosure. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the present disclosure being indicated by the appended claims, and not limited to the foregoing description.

It will be appreciated by those skilled in the art that various modifications and alterations of the present disclosure can be made without departing from the broad scope of the appended claims. Some of these have been discussed above and others will be apparent to those skilled in the art. The following examples provide non-limiting embodiments of various configurations of the devices, assemblies, systems, and methods disclosed herein.

In Example 1, a vascular closure device configured to seal a puncture in an artery or vein may include a deployment assembly having a proximal end and a distal end opposite the proximal end. The closure device may also include a suture carried by the deployment assembly, and a footplate carried by the deployment assembly and coupled to the suture. The footplate may be configured to exit the distal end of the deployment assembly for deployment in the puncture. The closure device may also include a retraction assembly coupled to the footplate, the retraction assembly configured to, after deployment of the footplate, retract the footplate in a proximal direction.

In Example 2, a vascular closure device configured to seal a puncture in an artery or vein may include a deployment assembly having a proximal end and a distal end opposite the proximal end. The closure device may also include a suture carried by the deployment assembly and a footplate carried by the deployment assembly and coupled to the suture. The footplate may be configured to exit the deployment assembly for deployment in the puncture. The closure device may also include a tether coupled to the footplate, the tether configured to, after the footplate exits the deployment assembly, retract the footplate in a proximal direction.

In Example 3, a vascular closure device configured to seal a puncture in an artery or vein may include a deployment assembly having a proximal end and a distal end opposite the proximal end, along with a suture carried by the deployment assembly. The closure device may also include a footplate carried by the deployment assembly and coupled to the suture. The footplate may be configured to 1) exit the deployment assembly for deployment, and 2) retract in a proximal direction after deployment. The closure device may also include a guide member having an elongated body and a footplate engagement member configured to abut the footplate. After deployment of the footplate, abutment of the footplate engagement member against the footplate may cause the footplate to pivot for retraction in the proximal direction.

In Example 4, the vascular closure device of any one or any combination of Examples 1-3 may be configured such that the retraction assembly includes a tether coupled to the footplate.

In Example 5, the vascular closure device of any one or any combination of Examples 1, 2, or 4 may be configured such that the retraction assembly includes a guide member engaged with the footplate.

In Example 6, the vascular closure device of one or both of Examples 2 or 4 may be configured such that the tether is a filament.

In Example 7, the vascular closure device of one or both of Examples 2 or 4 may be configured such that the tether is a wire.

In Example 8, the vascular closure device of one or both of Examples 2 or 4 may be configured such that the tether is an elongate shaft.

In Example 9, the vascular closure device of one or both of Examples 2 or 4 may be configured such that the tether extends through the deployment assembly.

In Example 10, the vascular closure device of one or both of Examples 2 or 4 may be configured such that the tether extends alongside the deployment assembly.

In Example 11, the vascular closure device of any one or any combination of Examples 1-10 may be configured such that the footplate includes an engagement member, portion, or feature that is coupled to a distal end of the tether.

In Example 12, the vascular closure device of any one or any combination of Examples 1-11 may be configured to further include a guide member with a proximal end, a distal end, and a lumen that extends from the proximal end to the distal end, wherein the lumen is configured to receive a guidewire therethrough.

In Example 13, the vascular closure device of one or both of Examples 3 or 12 may be configured such that the footplate includes an aperture through which the distal end of the guide member extends.

In Example 14, the vascular closure device of any one or any combination of Examples 3, 12 and/or 13 may be configured such that the guide member includes a footplate engagement member, where retraction of the tether and abutment of the footplate engagement member with a proximal surface of the footplate causes a trailing end of the footplate to pivot back toward the distal end of the deployment assembly.

In Example 15, the vascular closure device of Example 14 may be configured such that advancement of the guide member in a distal direction until the footplate engagement member abuts the proximal surface of the footplate causes the footplate to pivot for retraction toward the distal end of the deployment assembly in a distal direction.

In Example 16, the vascular closure device of any one or any combination of Examples 3 and 12-15 may be configured such that the guide member includes an advancement engagement member configured to advance the guide member in the proximal direction, when a force is applied to the advancement engagement member.

In Example 17, the vascular closure device of any one or any combination of Examples 2, 4 and 12-16 may be configured to further include an actuator configured to pull the tether in a proximal direction in order to retract at least the footplate in a proximal direction that is opposite a distal direction.

In Example 18, the vascular closure device of Example 17 may be configured such that the actuator is a push-pull member.

In Example 19, the vascular closure device of Example 17 may be configured such that the actuator is a rotatable knob.

In Example 20, the vascular closure device of Example 17 may be configured such that the actuator is a rotatable lever.

In Example 21, the vascular closure device of Example 17 may be configured such that the actuator is a slide.

In Example 22, the vascular closure device of any one or any combination of Examples 1-21 may be configured to further include a sealing unit that includes the footplate and a sealing plug coupled to the suture and positioned proximal to the footplate.

In Example 23, the vascular closure device of any one or any combination of Examples 1-22 may be configured to further include a movable lock along the suture, and a tamper slidable along the suture, the tamper configured to slide the movable lock into engagement with the sealing plug.

In Example 24, the vascular closure device of any one or any combination of Examples 1-23 may be configured such that the deployment assembly includes a release member and a delivery member, where either or both of the release member and delivery member are movable relative to the other to release the footplate from the deployment assembly.

In Example 25, the vascular closure device of any one or any combination of Examples 1-24 may be configured such that during retraction, a proximal end of the footplate is aligned toward the axis of the delivery device assembly.

In Example 26, a method for sealing a puncture in an artery or vein may involve inserting a distal end of a deployment assembly into the puncture of the artery or vein and causing a footplate of a sealing unit to exit out the distal end of the deployment assembly and into a lumen of the artery or vein. The method further may further involve determining a position of the footplate in the lumen of the artery or vein and retracting the footplate in a proximal direction toward the distal end of the deployment assembly, out of the lumen of the artery or vein.

In Example 27, the method of Example 26 further involves advancing a sealing plug out of the deployment assembly and retracting the sealing plug back toward the distal end of the deployment assembly.

In Example 28, the method of Example 26 may be implemented such that retracting the footplate in the proximal direction further involves retracting a tether coupled to the footplate.

In Example 29, the method of Example 28 may be implemented such that retracting the footplate back toward the distal end of the deployment assembly further involves advancing a footplate engagement member of a guide lumen or member against a proximal surface of the footplate, thereby causing the footplate to pivot for retraction in the proximal direction.

In Example 30, the method of Example 26 may further involve, after retracting the footplate in the proximal direction, readvancing the footplate in the distal direction toward the lumen of the artery or vein.

In Example 31, the method of any one or any combination of Examples 26-30 may further involve inserting an access sheath into the puncture of the artery or the vein, the access sheath having a proximal end that is positioned outside of the artery or the vein, a distal end that is located in the lumen of the artery or the vein, and a channel that extends from the distal end to the proximal end of the access sheath.

In Example 32, the method of any one or any combination of Examples 26-31 may be implemented such that inserting the distal end of the deployment assembly into the puncture of the artery or vein further involves inserting the deployment assembly into the channel of the access sheath until the distal end of the deployment assembly extends out of the distal end of the access sheath.

In Example 33, the method of any one or any combination of Examples 26-32 may be implemented such that the footplate is restrained by a release component and a delivery component of the deployment assembly, where causing the footplate to exit the distal end of the deployment assembly may further involve moving either or both of the release component and the delivery component relative to each other to release the footplate from the deployment assembly.

In Example 34, the method of any one or any combination of Examples 26-33 may be implemented such that retracting the footplate in the proximal direction involves retracting the proximal end of the footplate toward the distal end of the deployment assembly and out of the lumen of the artery or vein.

In Example 35, the method of any one or any combination of Examples 26-34 may be performed using a vascular closure device or component thereof according to any one or any combination of Examples 1-25.

The invention claimed is:

1. A vascular closure device configured to seal a puncture in an artery or vein, the vascular closure device comprising:
    a deployment assembly having a proximal end and a distal end opposite the proximal end;
    a suture carried by the deployment assembly;
    a footplate carried by the deployment assembly and coupled to the suture, wherein the footplate is configured to exit the distal end of the deployment assembly for deployment in the puncture;
    a retraction assembly coupled to the footplate, the retraction assembly configured to, after deployment of the footplate, retract the footplate in a proximal direction and comprising:
        a tether;
        a guide member with a proximal end, a distal end, and a lumen that extends from the proximal end to the distal end, wherein the lumen is configured to receive a guidewire therethrough;
wherein
    the footplate includes an aperture through which the distal end of the guide member extends,
    the guide member includes a footplate engagement member extending outward from a body of the guide member and configured to abut the footplate, and
    retraction of the tether and abutment of the footplate engagement member with a proximal surface of the footplate causes a trailing end of the footplate to pivot back toward the distal end of the deployment assembly.

2. The vascular closure device of claim 1, wherein the tether is coupled to the footplate.

3. The vascular closure device of claim 2, wherein the tether comprises a filament.

4. The vascular closure device of claim 2, wherein the tether comprises a wire.

5. The vascular closure device of claim 2, wherein the tether extends through the deployment assembly.

6. The vascular closure device of claim 2, wherein the tether extends alongside the deployment assembly.

7. The vascular closure device of claim 2, wherein the footplate includes an engagement feature that is coupled to a distal end of the tether.

8. The vascular closure device of claim 1, wherein the guide member is engaged with the footplate.

9. The vascular closure device of claim 1, wherein advancement of the guide member in a distal direction until the footplate engagement member abuts the proximal surface of the footplate causes the footplate to pivot for retraction toward the distal end of the deployment assembly in a distal direction.

10. The vascular closure device of claim 9, wherein the guide member includes an advancement engagement member extending outward from the body of the guide member and configured to advance the guide member in the proximal direction, when a force is applied to the advancement engagement member.

11. The vascular closure device of claim 10, further comprising an actuator configured to pull the tether in a proximal direction in order to retract at least the footplate in a proximal direction that is opposite a distal direction.

12. The vascular closure device of claim 11, wherein the actuator comprises a push-pull member, a rotatable knob, a rotatable lever, or a slide.

13. The vascular closure device of claim 1, further comprising a sealing unit that includes the footplate and a sealing plug coupled to the suture and positioned proximal to the footplate.

14. The vascular closure device of claim 1, further comprising a movable lock positioned along the suture, and a tamper slidable along the suture, the tamper configured to slide the movable lock into engagement with the sealing plug.

15. The vascular closure device of claim 1, wherein the deployment assembly includes a release member and a delivery member, and wherein either or both of the release member and delivery member are movable relative to the other to release the footplate from the deployment assembly.

16. The vascular closure device of claim 15, wherein during retraction, a proximal end of the footplate is aligned toward an axis of the deployment assembly.

* * * * *